(12) United States Patent
Peltola et al.

(10) Patent No.: US 10,828,509 B2
(45) Date of Patent: Nov. 10, 2020

(54) OPTIMIZING RADIATION DOSE TO OVERLAPPING STRUCTURES

(71) Applicant: Varian Medical Systems International AG, Cham (CH)

(72) Inventors: Jarkko Peltola, Tuusula (FI); Janne Nord, Espoo (FI); Yves Archambault, St Eustache (CA); Ramin Baghaie, Espoo (FI); Emmi Ruokokoski, Helsinki (FI)

(73) Assignee: Varian Medical Systems International AG, Cham (CH)

( * ) Notice: Subject to any disclaimer, the term of this patent is extended or adjusted under 35 U.S.C. 154(b) by 268 days.

(21) Appl. No.: 15/895,892

(22) Filed: Feb. 13, 2018

(65) Prior Publication Data
US 2019/0247676 A1 Aug. 15, 2019

(51) Int. Cl.
*A61N 5/10* (2006.01)
*G16H 20/40* (2018.01)

(52) U.S. Cl.
CPC .......... *A61N 5/1038* (2013.01); *A61N 5/103* (2013.01); *A61N 5/1031* (2013.01); *A61N 5/1036* (2013.01); *A61N 5/1045* (2013.01); *A61N 5/1047* (2013.01); *A61N 5/1077* (2013.01); *G16H 20/40* (2018.01)

(58) Field of Classification Search
CPC .... A61N 5/103–1039; A61N 2005/1032–1041
See application file for complete search history.

(56) References Cited

U.S. PATENT DOCUMENTS

| | | | |
|---|---|---|---|
| 6,052,430 A * | 4/2000 | Siochi | A61N 5/1042 378/152 |
| 8,502,177 B2 | 8/2013 | Bert et al. | |
| 9,586,058 B2 | 3/2017 | Bert et al. | |
| 10,220,222 B2 | 3/2019 | Popple | |
| 10,384,080 B2 | 8/2019 | Eriksson | |
| 2010/0195890 A1 | 8/2010 | Berlinger et al. | |

(Continued)

FOREIGN PATENT DOCUMENTS

| | | |
|---|---|---|
| CN | 102202733 A | 9/2011 |
| CN | 102227236 A | 10/2011 |

(Continued)

OTHER PUBLICATIONS

Chen et al., "Multi Criteria Optimization Informed VMAT Planning", Medical dosimetry, vol. 39, No. 1, 2014, 20 pages.

(Continued)

*Primary Examiner* — Catherine B Kuhlman
(74) *Attorney, Agent, or Firm* — Kilpatrick Townsend & Stockton LLP

(57) ABSTRACT

In radiation therapy, treatment objectives applicable to different identified structures in a patient's body (e.g., a target structure and an organ at risk (OAR)) may conflict due to overlap between the structures. Automated systems and methods can detect and resolve such conflicts. For example, a set of modified regions that do not overlap with each other can be defined, and a modified treatment objective for each modified region can be determined based on the original treatment objectives. The modified regions and modified treatment objectives can be used in treatment planning processes.

22 Claims, 13 Drawing Sheets

(56) References Cited

U.S. PATENT DOCUMENTS

| | | | |
|---|---|---|---|
| 2011/0272600 A1 | 11/2011 | Bert et al. | |
| 2013/0289332 A1* | 10/2013 | Purdie | A61N 5/1039 600/1 |
| 2015/0095043 A1* | 4/2015 | Cordero Marcos | A61N 5/1031 705/2 |
| 2016/0008630 A1 | 1/2016 | Vaitheeswaran et al. | |
| 2016/0059037 A1* | 3/2016 | Bender | A61N 5/1031 600/1 |
| 2018/0099151 A1* | 4/2018 | Sullivan | A61B 6/032 |
| 2018/0154177 A1* | 6/2018 | Bzdusek | A61N 5/1031 |

FOREIGN PATENT DOCUMENTS

| | | |
|---|---|---|
| CN | 106535991 A | 3/2017 |
| JP | 2003070921 A | 3/2003 |
| JP | 2016506789 A | 3/2016 |
| JP | 2016540598 A | 12/2016 |
| WO | 2014122567 | 8/2014 |
| WO | 2016198979 A1 | 12/2016 |

OTHER PUBLICATIONS

Djemil, "Pinnacle Auto-Planning", Cleveland Clinic, Apr. 29, 2016, 37 pages.

Monz et al., "Pareto Navigation-Algorithmic Foundation of Interactive Multi-Criteria IMRT Planning", Physics in Medicine and Biology, vol. 53, No. 4, Feb. 21, 2008, pp. 985-998.

European Application No. EP19156500.1, "Extended European Search Report", dated Jun. 17, 2019, 7 pages.

Japanese Application No. JP2019-022509, "Notice of Decision to Grant", dated Feb. 3, 2020, 1 page.

China International Application No. 201910109962.3, Office Action, dated Jul. 27, 2020, 5 pages.

* cited by examiner

OPTIMIZING RADIATION DOSE TO OVERLAPPING STRUCTURES

BACKGROUND

The present disclosure relates generally to treatment planning for radiation therapy and more specifically to techniques for optimizing radiation dose in instances where two or more structures with conflicting treatment objectives overlap.

In general, radiation therapy consists of the use of ionizing radiation to treat living tissue, usually tumors. Many different types of ionizing radiation are used in radiation therapy, including high-energy x-rays, electron beams, and proton beams. The process of administering radiation therapy to a patient can be similar across different types of radiation. Typically, an external-beam radiation treatment system is used. Such systems provide a linear accelerator that produces a beam of the desired type at a beam source and collimators including a multileaf collimator (MLC) to shape the beam that emerges from the beam source. The beam delivery system (including the beam source and collimators) is generally mounted on a movable gantry that can be moved around a treatment couch on which a patient is placed, allowing the radiation beam to be delivered from different angles relative to the patient.

Systems of this kind are used for various treatment options. One option is intensity-modulated radiotherapy (IMRT), in which the beam source is positioned at a desired angle, and the MLC is modulated to control the dose received by different tissues. During a treatment session, the beam source and/or the MLC may be repositioned, allowing radiation to be delivered from different angles. In IMRT, the beam source remains stationary while radiation is being delivered. Another treatment option is volumetric modulated arc therapy (VMAT), in which the beam source traverses an arc around the patient while delivering radiation. In both IMRT and VMAT, the overarching goal is to deliver a therapeutically effective dose of radiation (typically a high and uniform dose) to a target volume (typically a tumor) within the patient's body while minimizing the dose delivered to surrounding tissues (in particular, healthy organs or tissues that may be located close to the target volume).

Effective radiation therapy requires treatment planning to determine machine parameters that will optimally achieve the overarching goal. In the case of IMRT, a treatment plan may specify machine parameters such as positions of the beam source and collimators (including MLC leaf settings), beam intensity (e.g., dose rate), and duration of exposure (also referred to as "beam-on time"); the plan may include multiple control points, each defined by a set of machine parameters. In the case of VMAT, a treatment plan may specify all of the same machine parameters as in IMRT, plus additional parameters defining an arc to be traversed and in some instances speed of traversing the arc. During treatment, a treatment plan can be used to control operation of the radiotherapy system, and operating the radiotherapy system according to the treatment plan results in delivering a desired dose distribution to the patient.

Treatment planning is usually approached via the "inverse" problem of determining the optimal combination of machine parameters—such as beam intensity, beam shaping, beam direction(s), exposure duration—to deliver a desired total radiation dose to the target volume (or multiple target volumes) while minimizing the dose delivered to nearby organs or tissues (often referred to as "organs at risk," or "OAR"). The desired radiation doses can be expressed as a set of treatment objectives, and a cost function can be defined to quantify a difference between a predicted radiation dose and the set of treatment objectives. This cost function allows a practitioner to compare different treatment options.

SUMMARY

Among the challenges of treatment planning is the problem of overlap between different structures (or regions) having incompatible treatment objectives. For example, a target structure (a region of tissue to be treated with radiation) can overlap with one or more organs at risk (which can include nearby organs or tissues and/or healthy portions of an organ or tissue in which the target structure is present). The treatment objectives typically require that the dose delivered to the target structure be within a range between a maximum dose and a minimum dose and that the dose be as uniform as possible. The treatment objectives typically also require that the dose delivered to the OAR structure not exceed a prescribed upper limit. This upper limit is generally lower than the minimum dose for the target structure. Where there is overlap between the target structure and an OAR, a "conflict" between treatment objectives is said to exist if it is not possible to satisfy both treatment objectives in the overlap region. (While the present description uses instances of conflict between a target structure and an OAR as an example, it should be understood that other instances of conflict may occur, such as where two target structures having conflicting treatment objectives overlap with each other or where two OARs having conflicting treatment objectives overlap with each other.)

Certain embodiments of the present invention relate to automated techniques for resolving conflicts between treatment objectives when overlap exists between different structures having incompatible treatment objectives. By way of example, consider the case where a target structure overlaps with an OAR. It is assumed that the target structure and the OAR have been identified, e.g., using conventional techniques such as marking the structures on an image of the relevant portion of the patient's body, and that treatment objectives have been specified for the target structure and the OAR. A computer system executing appropriate program code can detect a geometric overlap between the target structure and the OAR and detect that a conflict between treatment objectives exists, such that both objectives cannot be satisfied within the overlap region. In response to this determination, the computer system can define a margin around one of the structures, where the margin provides a region where the dose should ramp up from the upper limit of the OAR dose to at least the minimum dose for the target region). In a typical instance, the margin is defined around the target structure (so that a portion of the margin extends into the OAR); however, in some instances, an OAR may be assigned a higher priority, and the margin can instead be defined around the OAR, with a portion of the margin extending into the target structure. In some embodiments, the margin can be defined automatically, e.g., based on beam type, location of the target structure within the patient's body, and/or other considerations, examples of which are described below. The computer system can redefine the regions of interest in a manner that allows the conflict to be resolved. In some embodiments, the regions of interest can be redefined to include modified regions that do not overlap with each other, such as an "OAR-only" region that includes the portion of the OAR that does not overlap with the target structure or the margin; a "target-only" region that includes the portion of the target structure that does not overlap with the OAR; an "OAR/margin" overlap region that includes the portion of the OAR that overlaps with the margin; and an "OAR/target" overlap region that includes the portion of the OAR that overlaps with the target structure. The computer system can then define a modified treatment objective for each modified region. In some cases, the modified treatment objectives defined for the modified regions that do not include overlapping structures (e.g., the OAR-only and target-only regions) may correspond to the originally-specified treatment objectives for the OAR and target structure. For the modified regions that include overlapping structures (e.g., the OAR/margin and OAR/target regions), new treatment objectives may be generated based on the originally-specified treatment objectives for the OAR and the target structure. The particular technique for generating new treatment objectives may depend on the originally-specified treatment objectives, and in some instances, the treatment objectives for the non-overlap modified regions (e.g., the OAR-only and target-only regions) may also be modified. Examples are described below. The modified regions and modified treatment objectives can replace the original structures and original treatment objectives in a treatment planning process.

Similar techniques can be applied in other situations where overlapping structures have conflicting treatment objectives, such as where two target structures having conflicting treatment objectives overlap or where two OARs having conflicting treatment objectives overlap. In some embodiments, more than two structures with conflicting treatment objectives may overlap, and the computer system can define modified regions from the set of overlapping structures and determine a modified treatment objective for each modified region.

The following detailed description, together with the accompanying drawings, provides a better understanding of the nature and advantages of the claimed invention.

DEFINITIONS

Figure 1:
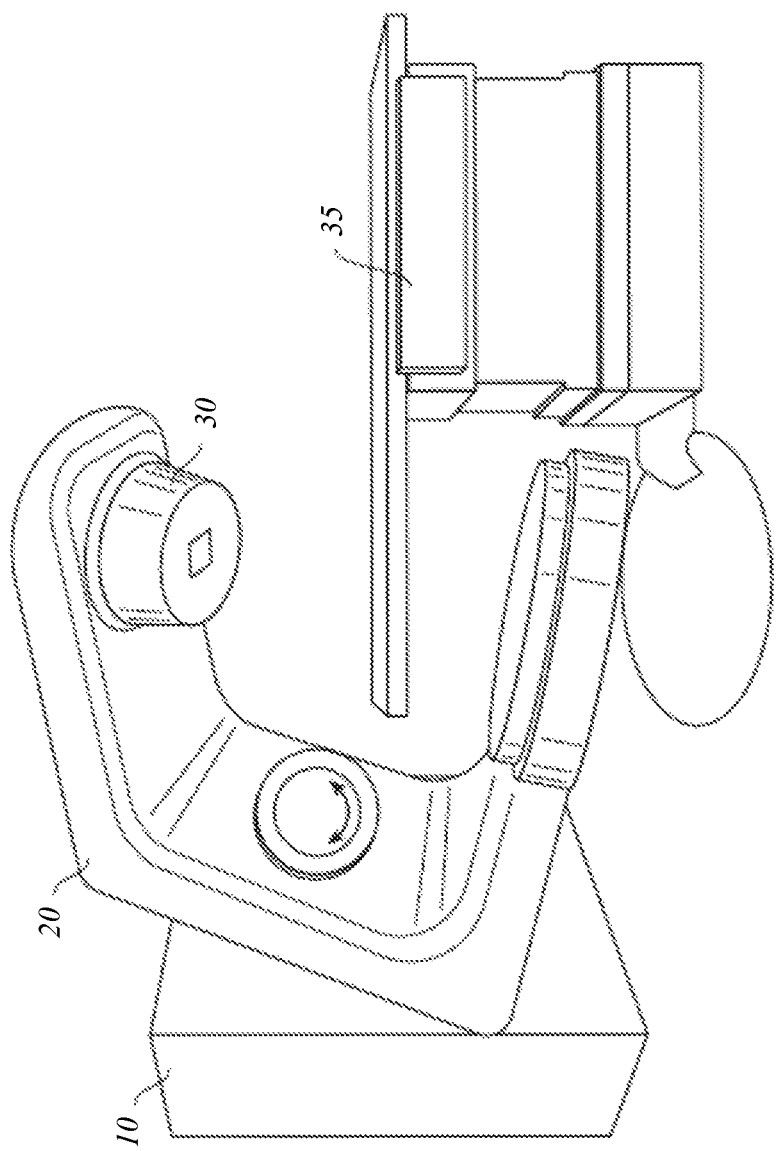
FIG. 1 shows a perspective view of a radiation treatment system that may be used in connection with an embodiment of the present invention.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" refer to tissue intended to receive a therapeutic prescribed dose. The irradiated volume is generally larger than the target volume and may include organs or tissues that are not intended to receive a therapeutic dose. Such organs or tissues are sometimes referred to as "organs at risk" (OAR).

A "radiation treatment plan" (also referred to as a "treatment plan" or "plan") can include a dose distribution, machine parameters for achieving the dose distribution for a given patient, and information about the given patient. A "dose distribution" provides information about the variation in the dose of radiation with position. A dose distribution can be represented in many formats, e.g., a dose volume histogram (DVH) or a dose matrix. A DVH can summarize three-dimensional (3D) dose distributions in a graphical format, e.g., where the horizontal axis is the dose (e.g., in units of grays (Gy)) absorbed by a particular volume or structure (which can be the target volume, an OAR, or any other well-defined volume) and the vertical axis is a volumetric percentage. In a differential DVH, the height of a bar at a particular dose indicates the volumetric percentage of the volume in question that receives the particular dose. In a cumulative DVH, the height of a bar at a particular dose represents the volumetric percentage of the volume in question that receives greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can show the dose that each part of the body receives.

A "dose prediction model" receives patient data and machine parameters and outputs a dose distribution that is predicted to be obtained. Different types of radiation treatments can have different models. The patient data can include diagnostic information (e.g., general tumor location or stage information) and geometric information (e.g., the spatial geometry of the tumor and of other organs in the patient). A particular model can have an accuracy (reliability) associated with the predicted dose distribution. The accuracy can be determined from a set of test radiation treatment plans whose dose distribution has been determined via other means (e.g., by optimizing a cost function). For example, the accuracy can be determined based on how well the model predicts the actual dose distributions obtained by optimizing a cost function.

"Monitor unit" (MU) is a measure of machine output from a clinical accelerator for radiation therapy such as a linear accelerator. Monitor units are measured by monitor chambers, which are ionization chambers that measure the dose delivered by a beam and are built into the treatment head of radiotherapy linear accelerators. Linear accelerators are calibrated to give a particular absorbed dose under particular conditions, although the definition and measurement configuration will vary between centers.

Two common definitions of monitor units are: (1) the monitor chamber reads 100 MU when an absorbed dose of 1 gray (100 rads) is delivered to a point at the depth of maximum dose in a water-equivalent phantom whose surface is at the isocenter of the machine (e.g., at 100 cm from the source for a typical machine) with a field size at the surface of 10 cm×10 cm; and (2) the monitor chamber reads 100 MU when an absorbed dose of 1 Gy (100 rad) is delivered to a point at a given depth in the phantom with the surface of the phantom positioned so that the specified point is at the isocenter of the machine and the field size is 10 cm×10 cm at the isocenter.

Some linear accelerators are calibrated using source-to-axis distance (SAD) instead of source-to-surface distance (SSD), and calibration (monitor unit definition) may vary depending on hospital custom. Early radiotherapy was performed using "constant SSD" treatments, and so the definition of monitor unit was adopted to reflect this calibration geometry. Modern radiotherapy is performed using isocentric radiation treatment plans, so newer definitions of the monitor unit are based on geometry at the isocenter based on the source-to-axis distance (SAD).

The term "spatial point" used in this disclosure in relation to a treatment field refers to a geometrical point associated with a set of values for treatment axes coordinates of an external-beam radiation treatment system. A spatial point is defined by the position of the isocenter, the position and angles of the patient support, the gantry angle, the collimator angle, and the position of each MLC leaf. The term "control point" refers to a parametrical point of a radiation treatment field that includes spatial information about the treatment axes and may also specify collimator settings, beam intensity or dose rate (e.g., using MU count and/or the related concept of the meterset weight), and/or speed of motion of the beam source (including a speed of a movable gantry supporting the beam source).

DETAILED DESCRIPTION

Radiation Therapy Systems

External beam therapy (EBT), also called external radiation therapy, is a method for delivering a beam or several beams of photons (e.g., x-rays) or other particles (e.g., protons, electrons) to a patient's tumor. Beams are generated outside the patient and are targeted at the tumor site.

Figure 2:
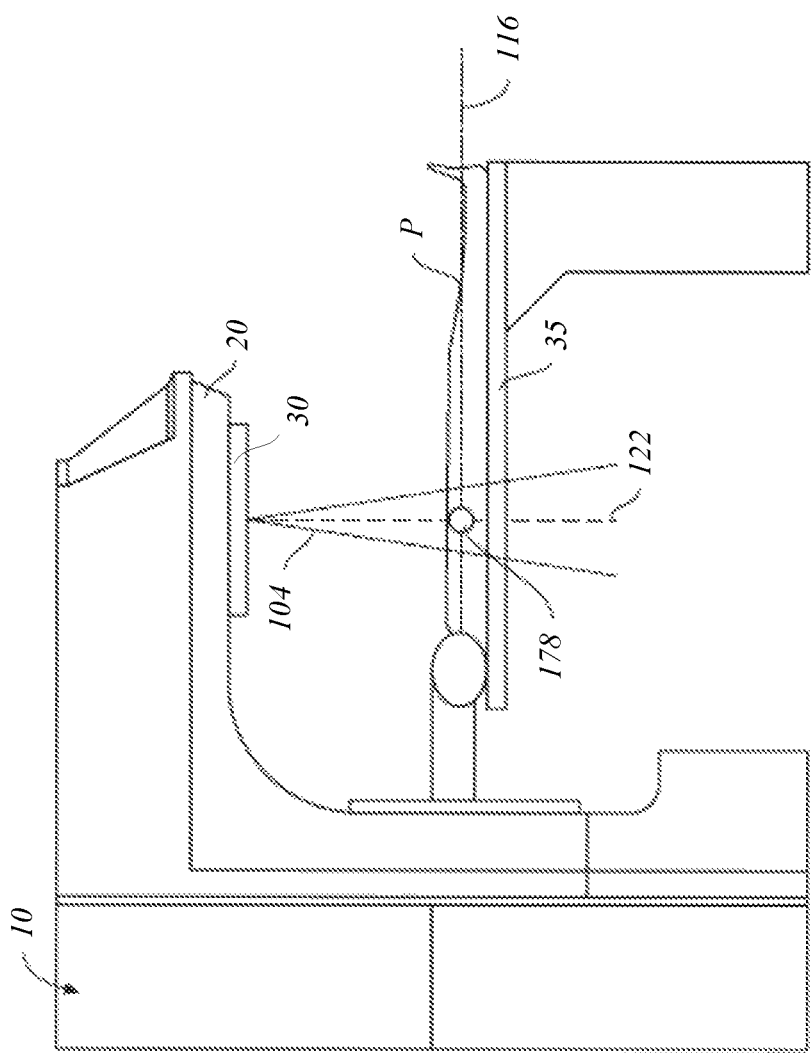
FIG. 2 shows a side view of the radiation treatment system of FIG. 1.

FIGS. 1 and 2 depict a radiation treatment system 100 that may be used in connection with an embodiment of the present invention. FIG. 1 shows a perspective view of radiation treatment system 100 (in this case incorporating a linear accelerator). Radiation treatment system 100 may be capable of generating either a particle beam (e.g., electrons or protons) or a photon beam (e.g., x-rays) for use in the radiotherapy treatment of a patient on a treatment couch 35. For purposes of the present description, x-ray irradiation will be assumed. However, it will be appreciated by those skilled in the art that the same principles apply to other systems, including electron beam systems and heavy-ion (e.g., proton) beam systems.

Stand 10 supports a rotatable gantry 20 with a treatment head 30. Next to stand 10 there is arranged a control unit (not shown) which includes control circuitry for controlling the different modes of operation of radiation treatment system 100. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

FIG. 2 shows a somewhat more detailed side view of radiation treatment system 100. A patient P is shown lying on treatment couch 35. X-rays formed as described above are emitted from the metal target in treatment head 30 in a divergent beam 104. Typically, a patient plane 116, which is perpendicular to the page in FIG. 2, is positioned about one meter from the x-ray source (e.g., the metal target), and the axis of gantry 20 is located in patient plane 116, such that the distance between the target in treatment head 30 and isocenter 178 remains constant when gantry 20 is rotated. Isocenter 178 is a point located at the intersection between patient plane 116 and the central axis of beam 122. Patient P can be positioned on treatment couch 35 such that a treatment volume to be irradiated is located about isocenter 178.

Figure 3:
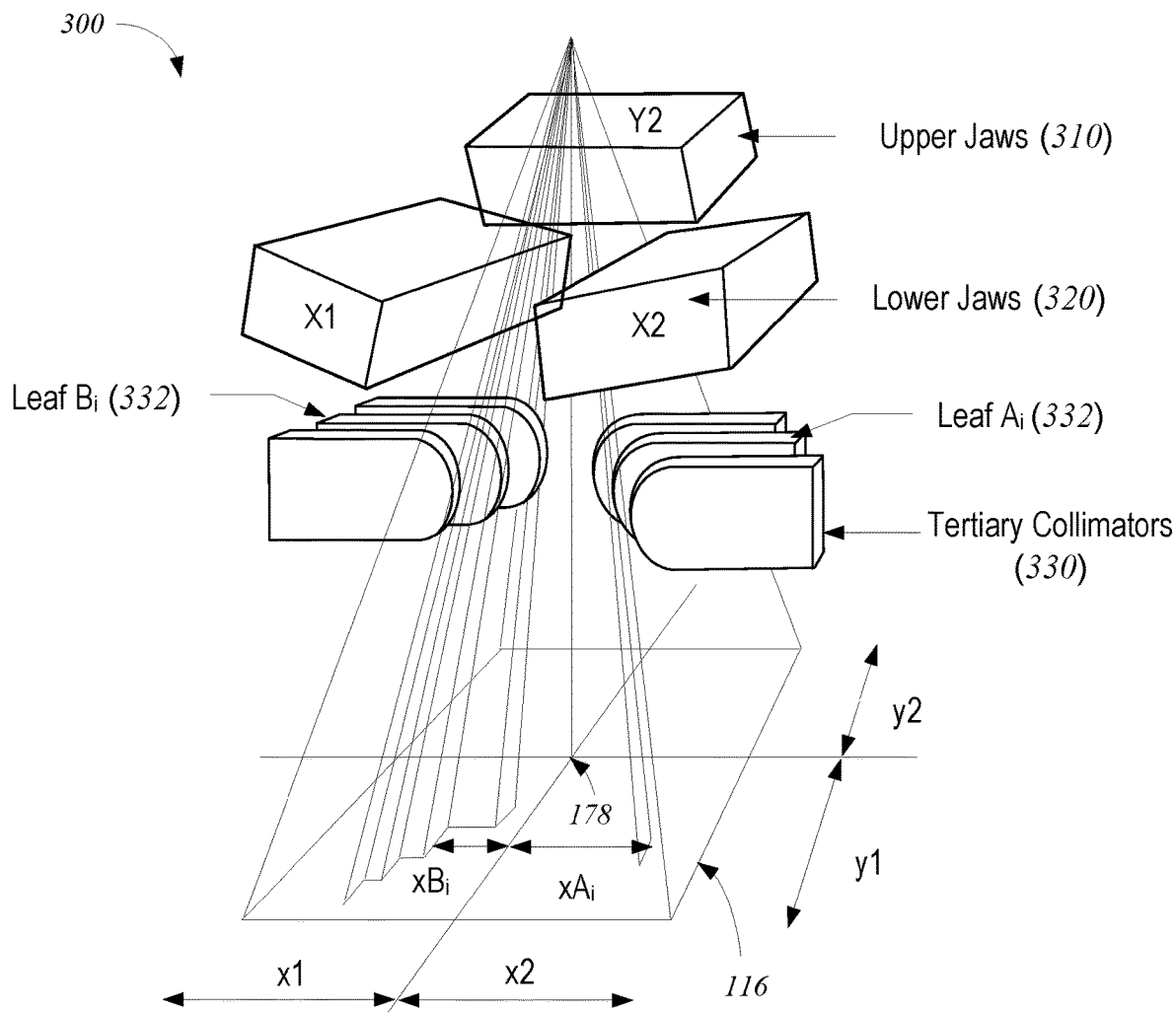
FIG. 3 shows schematically a photon collimation system that may be included in the radiation treatment system of FIG. 1.

In some embodiments, the beam can be shaped, e.g., using configurable collimators, to optimize the dose distribution to selectively target a tumor or other diseased tissue. FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multileaf collimator (MLC) 330. The field dimensions in patient plane 116 and the location of isocenter 178 are indicated. Upper jaws 310, lower jaws 320, and leaves 332 of MLC 330 are made at least partially of an x-ray blocking material and are positioned in treatment head 30 (shown in FIG. 2) to define the width of the x-ray beam at patient plane 116. Typically, jaws 310 and 320 are moveable and, when fully open, define a maximum beam width of about 40 cm×40 cm at patient plane 116. MLC 330 is positioned at the exit of treatment head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software.

Figure 4:
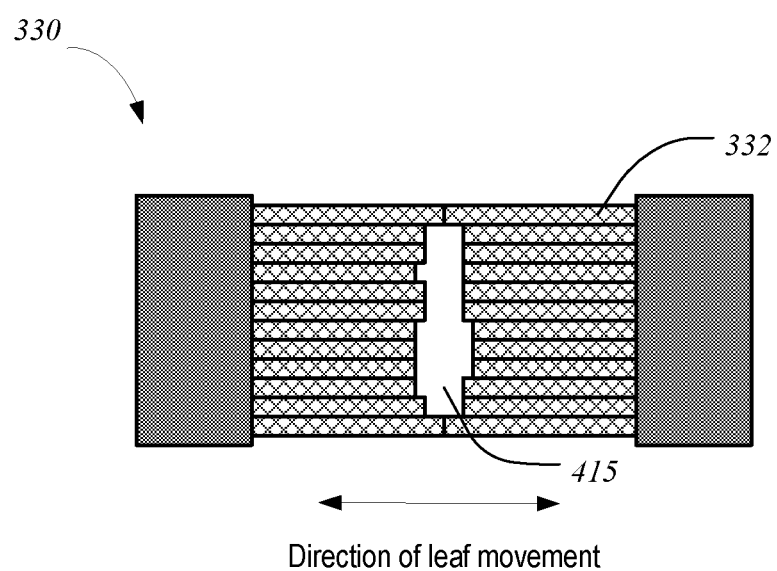
FIG. 4 shows an exemplary multileaf collimator plane that may be used in the photon collimation system of FIG. 3.

FIG. 4 shows an exemplary MLC plane having a plurality of leaves 332, arranged in opposing pairs, and an aperture 415 created by selected leaf movements. Radiation passes through and is shaped by aperture 415. Thus, MLC 330 can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to isocenter 178 in the treatment path of the x-ray beam, is defined by jaws 310 and 320, the leaf sequence of MLC 330, and the collimator angle, i.e., the angle at which MLC 330 sits in treatment head 30. In some embodiments, the position of jaws 310 and 320, the leaf sequence of MLC 330, and the collimator angle are all controllable machine parameters; in other embodiments, some of these parameters may be fixed.

Figure 5:
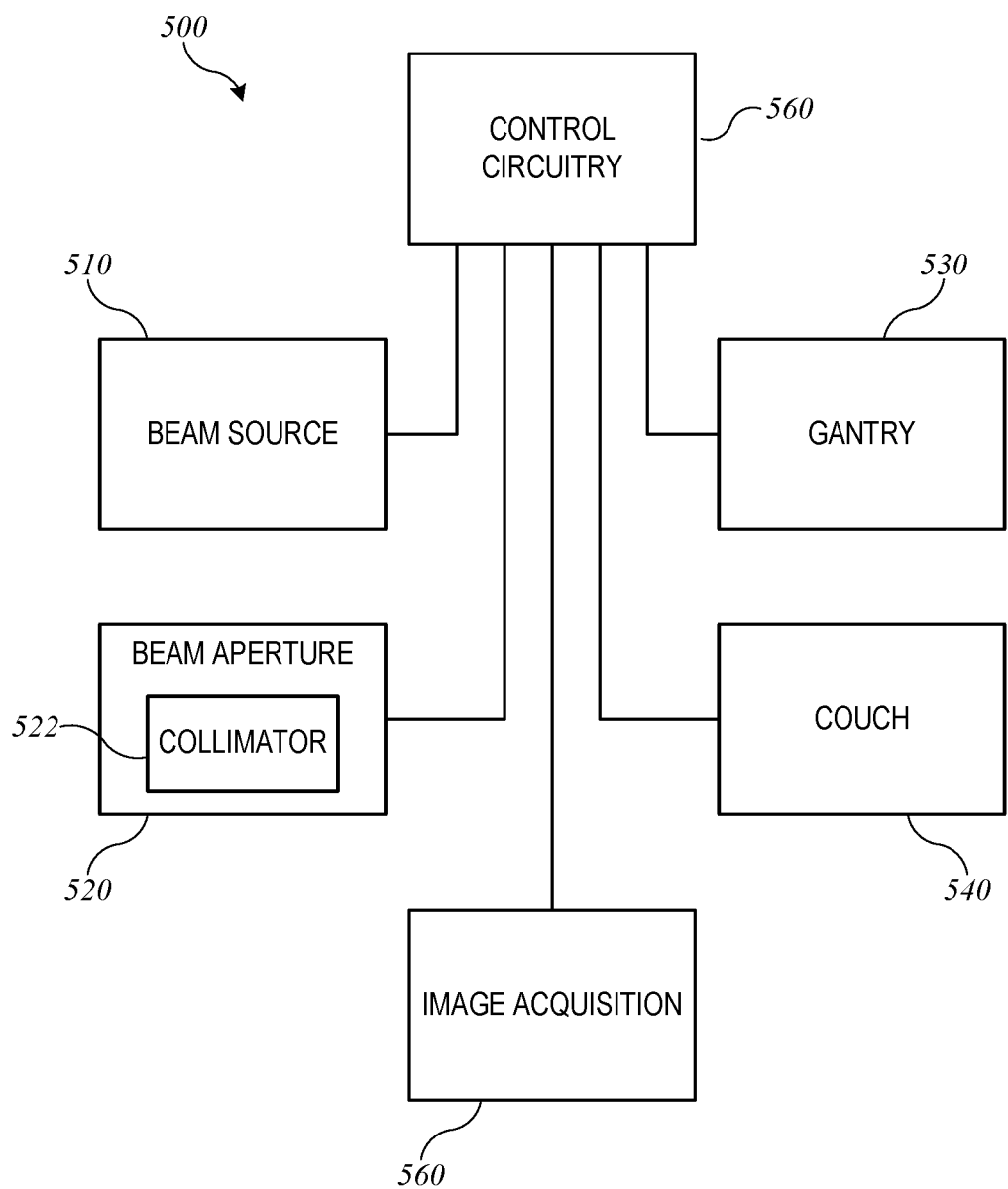
FIG. 5 shows a block diagram of an external-beam radiation treatment system that may be used in connection with the present invention.

FIG. 5 shows a block diagram of an external-beam radiation treatment system 500 implementing radiation treatment system 100 of FIGS. 1 and 2. Radiation treatment system 500 includes a beam source 510, a beam aperture 520, a gantry 530, and a couch 540. Beam source 510 is configured to generate a beam of therapeutic radiation. This beam of radiation may include x-rays, particles, or the like. Beam aperture 520 includes an adjustable multi-leaf collimator (MLC) 522, which can be an implementation of MLC 330 described above, for spatially filtering the radiation beam. Couch 540, which can be an implementation of treatment couch 35 of FIGS. 1 and 2, is configured to support and position a patient during treatment. Couch 540 may have six degrees of freedom (the translational offsets X, Y, and Z, and the rotation, pitch, and yaw), which may be treated as machine parameters.

Gantry 530, which can be an implementation of gantry 20, houses beam source 510 and beam aperture 520. Gantry 530 can be movable, e.g., rotatable, around a fixed axis, and volumetric modulated arc therapy (VMAT) treatment can be performed by rotating gantry 530 while beam source 510 is delivering beam. The arc to be traversed (e.g., starting and ending points) and/or speed of traversal can be treated as additional machine parameters.

In some embodiments, beam source 510 can be configured to generate imaging radiation as well as therapeutic radiation. Accordingly, radiation treatment system 500 may also include an image acquisition system 550 that comprises one or more imaging detectors mounted to gantry 530 (e.g., on an arm opposite beam aperture 520).

Radiation treatment system 500 further includes control circuitry 560 for controlling the operation of beam source 510, beam aperture 520, gantry 530, couch 540, and image acquisition system 550. Control circuitry 560 may include hardware, software, and memory for controlling the operation of these various components of radiation treatment system 500. Control circuitry 560 can comprise a fixed-purpose hard-wired platform or can comprise a partially or wholly-programmable platform. Control circuitry 560 can be configured to carry out various steps, actions, and other functions described herein. In some embodiments, control circuitry 560 may include a memory for receiving and storing a radiation treatment plan that defines the spatial points or control points of one or more treatment fields. Control circuitry 560 may then send control signals to the various components of radiation treatment system 500, such as beam source 510, beam aperture 520, gantry 530, and couch 540, to execute the radiation treatment plan. In some embodiments, control circuitry 560 may include an optimization engine to determine a radiation treatment plan; in other embodiments, an optimization engine can be provided in a separate computer system that delivers a radiation treatment plan to control circuitry 560 via a network interface or computer-readable storage medium.

Treatment Planning Overview

For therapeutically effective use of radiation treatment system 100 (or similar systems), it is generally desirable to develop a treatment plan prior to exposing a patient to radiation. During treatment planning, a practitioner identifies a set of treatment objectives specifying the radiation dose to be delivered to various relevant regions in a patient's body. The relevant regions generally include one or more target structures (where tumors or other tissue to be treated are present) and one or more organs at risk (OAR) (healthy tissues or structures that may be near enough to the target structure to be subjected to at least some radiation). For a target structure, the treatment objective is generally defined as a uniform and therapeutically effective ("high") dose across the entire structure. For an OAR, the treatment objective is generally defined as an upper limit, with the goal of minimizing radiation damage to healthy tissue. Based on the treatment objectives, a generalized cost function can be defined. For instance, a desired treatment outcome (i.e., meeting all of the treatment objectives) can be defined as a vector in a multidimensional space, where each component corresponds to a dose delivered to a particular volumetric element (voxel) within the patient's body. A cost function is defined to quantify a distance (in the multidimensional space) between the desired outcome and an alternative outcome. Euclidean or other distance metrics can be used, and different components of the outcome vector may be assigned different weights in the cost function. The optimum solution can be identified by finding an alternative solution that minimizes the cost function. For instance, a dose prediction model can be used to generate alternative outcomes for various combinations of adjustable machine parameters (e.g., beam intensity, beam aperture, MLC leaf sequence, duration of exposure, relative position of beam and patient), and the cost function can be computed for each alternative outcome. For purposes of the present disclosure, particular techniques for defining a cost function and identifying an alternative outcome that minimizes the cost function are not critical, and those skilled in the art will be aware of numerous such techniques.

Treatment Planning: Conflicting Treatment Objectives

Figure 6:
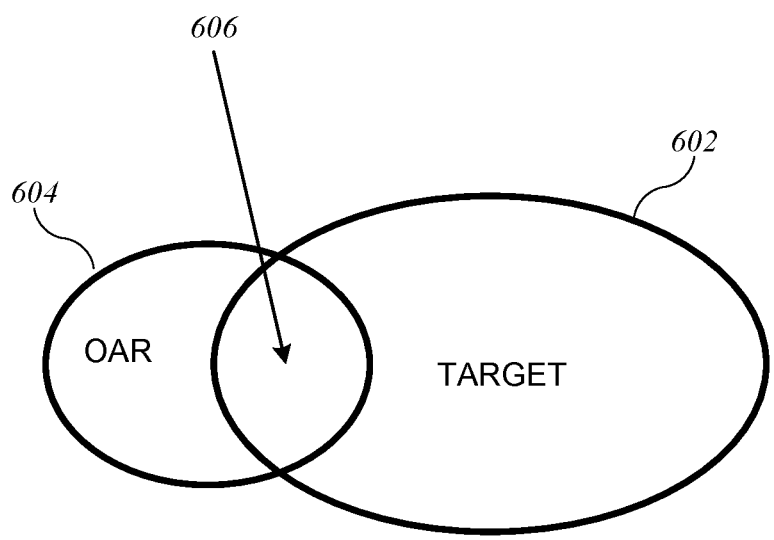
FIG. 6 is a simplified diagram illustrating a case where two treatment objectives conflict due to overlapping structures.

Certain embodiments of the present invention relate to establishing a set of treatment objectives for use in treatment planning, particularly in cases where two (or more) treatment objectives conflict. FIG. 6 is a simplified diagram illustrating a case where two treatment objectives conflict due to overlapping structures. Shown are a target structure 602 and an OAR 604, as seen in a plane transverse to an expected beam direction. In clinical practice, target structure 602 and OAR 604 may be identified, e.g., by a practitioner drawing the outlines of the structures on an image obtained by scanning the patient (e.g., using MM, X-Ray, CT scan or the like). Treatment objectives for target structure 602 and OAR 604 may also be specified by the practitioner.

As can be seen, target structure 602 and OAR 604 have an overlap region 606. Within this region, the treatment objectives may conflict; i.e., it may not be possible to satisfy both objectives at the same time. For instance, suppose that the treatment objective for target structure 602 specifies that 100% of the target volume should receive a dose between 50 Gy and 51 Gy, while the treatment objective for OAR 604 specifies that not more than 10% of the OAR volume should receive a dose more than 40 Gy. If overlap region 606 includes at least 10% of the volume of OAR 604, then it is not possible to satisfy both of these treatment objectives, and a conflict is said to exist.

Figure 7:
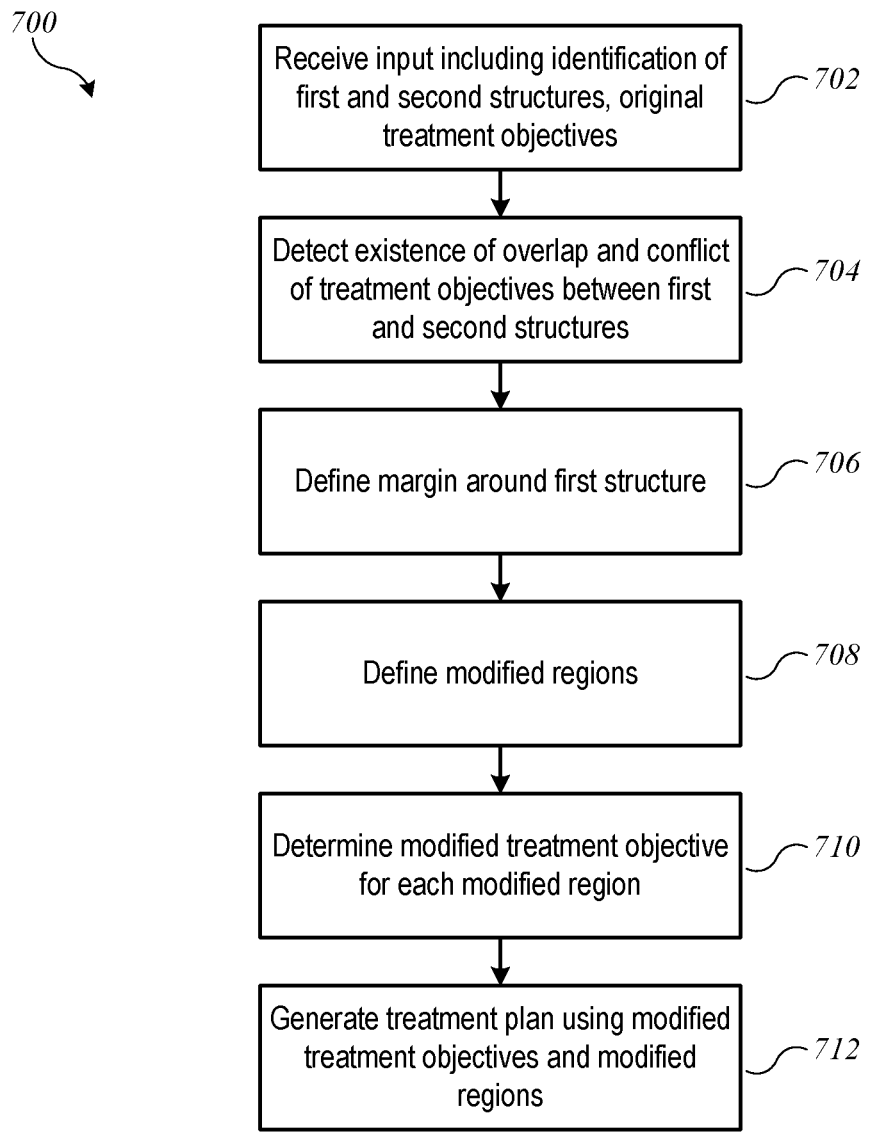
FIG. 7 is a flow diagram of a process for resolving conflicting treatment objectives according to an embodiment of the present invention.

FIG. 7 is a flow diagram of a process 700 for resolving conflicting treatment objectives according to an embodiment of the present invention. Process 700 can be performed in a computer system, e.g., using control circuitry 560 of radiation treatment system 500 (FIG. 5) or another computer system. For ease of understanding, process 700 will be described with specific reference to a case where the overlapping structures with conflicting treatment objectives are a target structure and an organ at risk; those skilled in the art with access to the present disclosure will recognize that process 700 can be applied more generally to any instance where a first structure and a second structure overlap and have conflicting treatment objectives.

Process 700 can begin at block 702, when input is received. The input can include identification of a first structure (e.g., target structure 602) and a second structure (e.g., OAR 604). The input can also include original treatment objectives for the first structure and the second structure. While the present description focuses on two structures that overlap, it is to be understood that the input can include identification of any number of structures (or regions) and associated treatment objectives, including multiple targets and/or multiple OARs, and process 700 can be applied wherever overlap exists between two or more structures or regions.

At block 704, process 700 can detect the existence of overlap (e.g., region 606) and a conflict of treatment objectives between the first and second structures. Detection of overlap and conflicts can be automatic and based on analysis of the input information. For instance, based on the input identifying target structure 602 and OAR 604, a boundary around each structure can be identified, and further analysis can identify areas (e.g., pixels or voxels) that are inside the boundaries of both structures. Once overlap is detected, process 700 can determine whether the treatment objectives for the overlapping structures conflict, e.g., by determining whether a minimum dose specified for target structure 602 exceeds a maximum or average dose specified for OAR 604. For purposes of this description, it is assumed that overlap and conflict are detected. In practice, it is possible that no overlap is present or that overlap is present but no conflict of treatment objectives is detected; in such a case, process 700 can exit, and treatment planning can continue, e.g., using conventional processes. Alternatively, even where no conflict of treatment objectives is detected, processing as described below can be used to refine the set of treatment objectives for the overlapping structures.

At block 706, process 700 can define a margin around one of the overlapping structures, e.g., target structure 602. The margin, which can be automatically defined without user input, can be an area or volume extending beyond the border of target structure 602 that allows for the radiation dose to ramp up from a low level to a high level desired for the target. More generally, a margin can be an area or volume extending beyond the border of a first structure that allows for the radiation dose to ramp up or down to a level desired for the first structure. In some embodiments, process 700 can choose one of the two overlapping structures as the structure around which a margin is defined based on priorities assigned to the structures. For instance, delivering high dose to the target structure is often a higher priority than protecting all of the OAR tissue, in which case the margin would be drawn around the target structure. However, in some instances, protecting the OAR may be a higher priority (e.g., where the OAR is the spinal cord or a portion thereof), and in that case the margin can be drawn around the OAR.

Figure 8A:
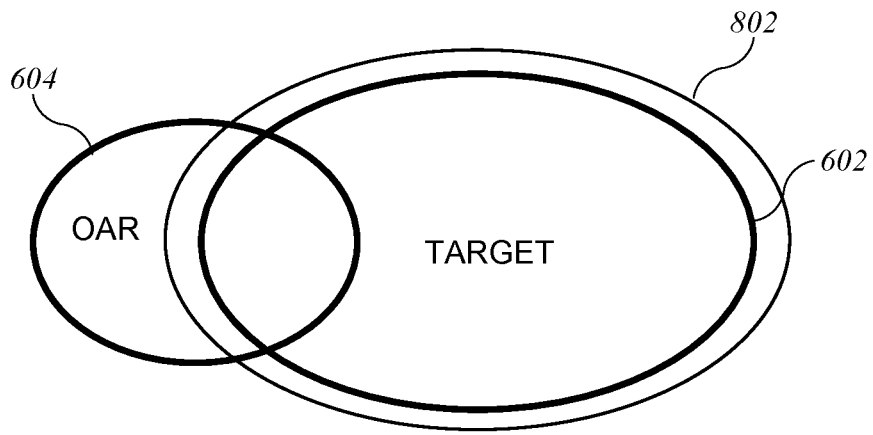
FIG. 8A shows an example margin defined around the target structure of FIG. 6 according to an embodiment of the present invention.

FIG. 8A shows an example margin 802 defined around target structure 602 of FIG. 6. In some embodiments, the margin can be defined statically; for instance, the margin can be 5 mm in the direction lateral to the beam axis and 3 mm in the direction along the beam axis (referred to as the longitudinal direction). In other embodiments, the margin can be defined dynamically based on the type of beam and/or other parameters of the radiation field. Examples of dynamically defining margins are described below.

Figure 8B:
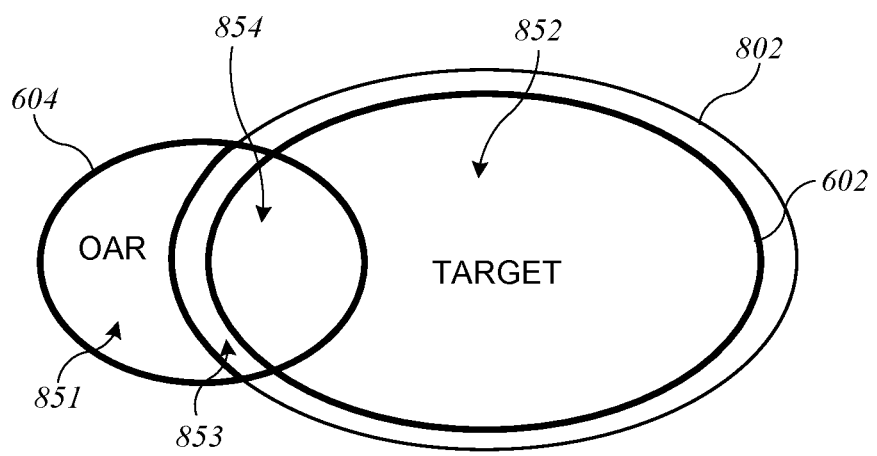
FIG. 8B shows an example in which the OAR and target structure of FIG. 6 are segmented into four modified regions according to an embodiment of the present invention.

At block 708, process 700 can define a set of modified regions based on the first and second structures and the margin. The modified regions are defined such that they do not overlap with each other. For instance, FIG. 8B shows an example in which OAR 604 and target structure 602 are segmented into four modified regions: (1) a first modified region ("OAR only" region 851) that includes the portion of OAR 604 that does not overlap with either margin 802 or target structure 602; (2) a second modified region ("target only" region 852) that includes the portion of target structure 602 (but not margin 802) that does not overlap with OAR 604; (3) a third modified region ("OAR/margin" overlap region 853) that includes the portion of OAR 604 that overlaps with margin 802; and (4) a fourth modified region ("OAR/target" overlap region 854) that includes the portion of OAR 604 that overlaps with target structure 602.

At block 710, process 700 can determine a modified treatment objective for each of the modified regions. In some embodiments, the modified treatment objective for one or more of the modified regions may be the same as one of the original treatment objectives. For example, for target-only region 852, the modified treatment objective can be the treatment objective that was originally identified for all of target structure 602. In overlap regions 853, 854, two different (and possibly conflicting) treatment objectives may apply, and new treatment objectives can be defined. In OAR-only region 851, the modified treatment objective can be the original treatment objective, or the original treatment may be modified in view of treatment objectives established for overlap regions 853, 854.

Various techniques can be used to define modified treatment objectives for the modified regions, and the particular technique may depend on how the treatment objectives were originally specified. The modification techniques can also take into account assumptions about how the original treatment objectives were determined. For instance, practitioners are generally aware of potential overlap between an OAR and a target structure and may define treatment objectives to allow the portion of the OAR that is nearest the target structure to receive a higher dose of radiation than would otherwise be desirable, in order to allow the entire target structure to receive a therapeutically effective dose. In defining modified treatment objectives, a maximum dose originally specified for the OAR as a whole can be selectively allocated toward the overlap regions while the maximum dose received by the OAR-only region is reduced. Examples of such selective allocation will now be described.

Figure 9:
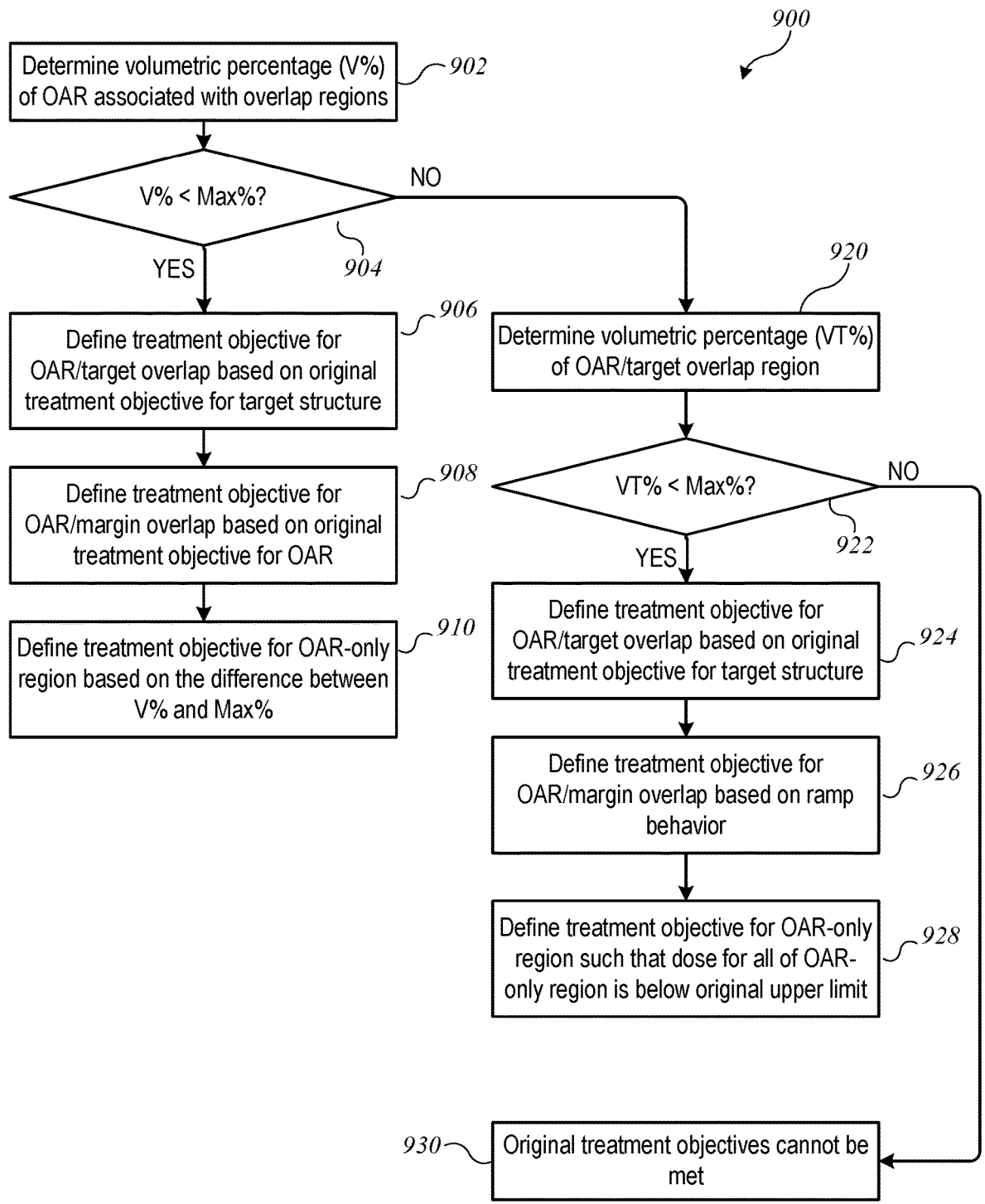
FIG. 9 shows a flow diagram of a process for determining modified treatment objectives when an original treatment objective specifies a volumetric limit for the OAR according to an embodiment of the present invention.

In one example, an original treatment objective for OAR 604 may specify the maximum (volumetric) percentage of OAR 604 (denoted herein as Max %) that should be allowed to receive a dose above an upper limit. For example, the original treatment objective for OAR 604 might be: "not more than 40% of the OAR should receive a dose above 40 Gy." FIG. 9 shows a flow diagram of a process 900 for determining modified treatment objectives when an original treatment objective specifies a volumetric limit for the OAR according to an embodiment of the present invention. Process 900 can be implemented, e.g., at block 710 of process 700. Process 900 assumes that a dose exceeding the original upper limit can be allowed in some or all of the OAR/target overlap region; dose limits in other regions are determined accordingly.

More specifically, at block 902, process 900 determines the (volumetric) percentage of OAR 604 that is assigned to overlap regions 853, 854; that percentage is denoted as V %. At block 904, a determination is made as to whether V % is less than (or equal to) the maximum percentage Max % specified in the original treatment objective. If so, then a dose above the original upper limit can be allowed in all of both OAR/target overlap region 854 and OAR/margin overlap region 853 without violating the original treatment objective. Accordingly, at block 906, a modified treatment objective for OAR/target overlap region 854 can be defined, e.g., based on the original treatment objective for target structure 602, allowing OAR/target overlap region 854 to receive a high dose of radiation. At block 908, a modified treatment objective for OAR/margin overlap region 853 can be defined, e.g., based on the original treatment objective for target structure 602. Since margin 802 is defined to allow a ramp-up effect, it may be desirable to set an upper limit for this region; for instance, a lower limit on the radiation dose originally specified for target structure 602 may be used as an upper limit for OAR/margin overlap region 853. At block 910, a modified treatment objective for OAR-only region 851 can be defined, e.g., based on the difference between V % and Max %. In other words, it is assumed that all of the portion of OAR 604 that is assigned to overlap regions 853, 854 will receive a dose over the originally-specified upper limit; this assumption plus the originally specified maximum percentage restricts the portion of OAR-only region 851 that can be exposed to a dose over the originally-specified limit. Once the modified treatment objectives are determined, process 900 can end.

If, at block 904, process 900 determines that V % exceeds Max %, further fine-tuning may be desired. Accordingly, at block 920, process 900 determines the (volumetric) percentage of OAR 604 that is assigned to OAR/target overlap region 854; that percentage is denoted as VT %. At block 922, process 900 determines whether VT % is less than (or equal to) the maximum percentage Max % specified in the original treatment objective. If so, then a dose above the originally-specified upper limit can be allowed in OAR/target overlap region 854 and some (but not all) of OAR/margin overlap region 853 without violating the original treatment objective for the OAR. Accordingly, at block 924, a modified treatment objective for OAR/target overlap region 854 can be defined, e.g., based on the original treatment objective for target structure 602, allowing OAR/target overlap region 854 to receive a high dose of radiation. At block 926, a modified treatment objective for OAR/margin overlap region 853 can be defined. For instance, based on the difference between VT % and Max %, an appropriate percentage of OAR/margin overlap region 853 can be permitted to receive a dose higher than the originally-specified upper limit for OAR 604. At block 928, a modified treatment objective for OAR-only region 851 can be defined. In this case, Max % has already been allocated to the overlap regions, and the modified treatment objective for OAR-only region 851 may specify that no part of OAR-only region 851 should receive a dose higher than the originally specified upper limit. Once the modified treatment objectives are determined, process 900 can end.

If, at block 922, process 900 determines that VT % exceeds Max %, then the situation is such that the original treatment objectives for the OAR and the target structure cannot both be satisfied (block 930); there is a choice to be made between providing a uniformly high dose to the entire target structure or keeping the dose to the OAR below the specified upper limit. In some embodiments, an error condition may result, with an alert to the practitioner (or other user operating a computer system on which process 900 executes) that one or the other of the original treatment objectives needs to be relaxed; the practitioner may adjust the treatment objectives accordingly. In other embodiments, process 900 can include additional logic to best approximate the treatment objectives given that satisfying both is not possible.

By way of numerical example, suppose that the original treatment objective for OAR 604 specifies that not more than 40% of the OAR should receive a dose above 40 Gy and the original treatment objective for target structure 602 specifies that 100% of target structure 602 should receive a dose of between 50 Gy and 51 Gy. Suppose that the volumes of OAR/margin overlap region 853 and OAR/target overlap region 854 add up to 25% of the total volume of OAR 604 (less than 40%). In this case the decision at block 904 of process 900 is Yes. At block 906, the modified treatment objective for OAR/target overlap region 854 can be defined as allowing all of OAR/target overlap region 854 to receive a dose higher than 40 Gy; for instance all of OAR/target overlap region 854 may be allowed to receive a dose up to 51 Gy, or the original treatment objective for target structure 602 can be applied to OAR/target overlap region 854. At block 908, the modified treatment objective for OAR/margin overlap region 853 can be defined as allowing all of OAR/margin overlap region 853 to receive a dose higher than 40 Gy. At block 910, there is a residual 15% (out of the original 40%) of the volume of OAR 604 that is not accounted for yet, and so the modified treatment objective for OAR-only region 851 can be defined as allowing up to 15% of the volume of OAR-only region 851 to receive a dose above 40 Gy. This set of modified treatment objectives is consistent with the original treatment objectives, in that if the modified treatment objectives are satisfied, no more than 40% of OAR 604 will receive a dose higher than 40 Gy.

Now suppose that the original treatment objectives are the same, but the volume of OAR/target overlap region 854 (VT %) is 35% of the total volume of OAR 604 and the volume of OAR/margin overlap region 853 is 10% of the total volume of OAR 604. In this case V % is 45%, which exceeds 40%, and the decision at block 904 is No. VT % is less than 40%, and the decision at block 922 is Yes. At block 924, the modified treatment objective for OAR/target overlap region 854 can be defined as allowing all of OAR/target overlap region 854 to receive a dose higher than 40 Gy. For instance all of OAR/target overlap region 854 may be allowed to receive a dose up to 51 Gy, or the original treatment objective for target structure 602 can be applied to OAR/target overlap region 854. At block 926, the treatment objective for OAR/margin overlap region 853 can be defined as allowing up to 50% of the volume of OAR/margin overlap region 853 (which is equal to 5% of the total volume of OAR 604 in this example) to receive a dose higher than 40 Gy. At block 928, the treatment objective for OAR-only region 851 can be defined as allowing none of OAR-only region 851 to receive a dose higher than 40 Gy. This set of modified treatment objectives is consistent with the original treatment objectives, in that if the modified treatment objectives are satisfied, no more than 40% of OAR 604 will receive a dose higher than 40 Gy.

Figure 10:
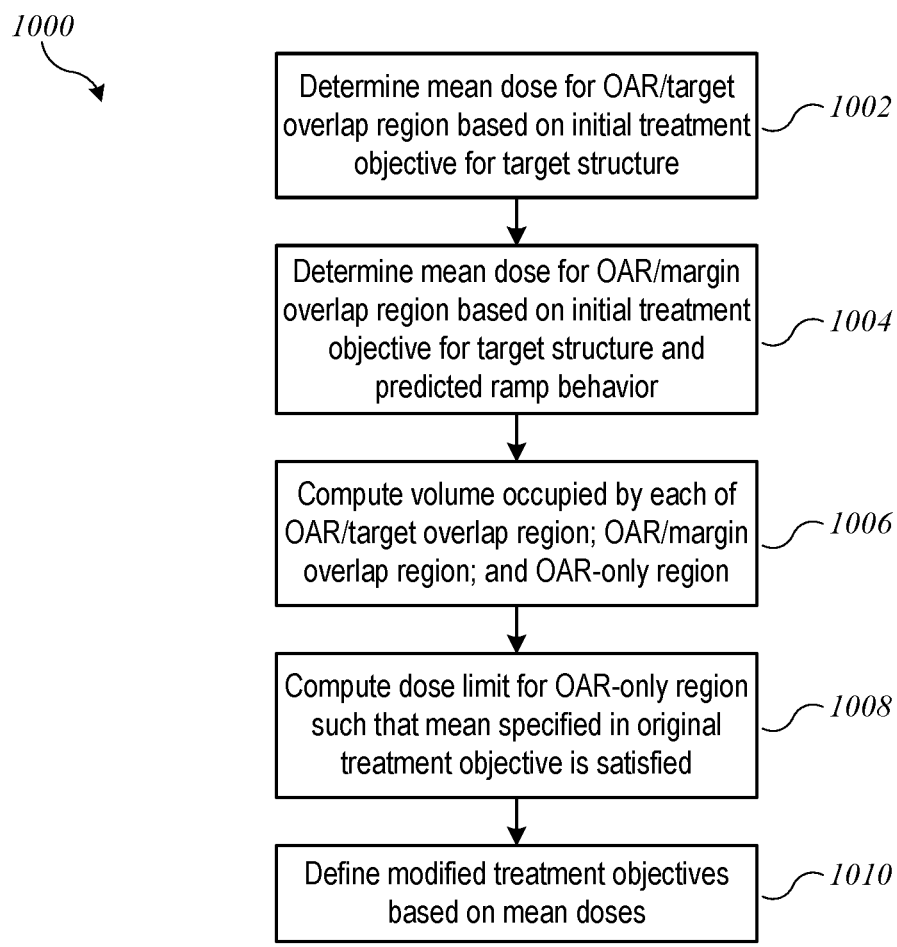
FIG. 10 shows a flow diagram of a process for determining modified treatment objectives when an original treatment objective specifies a mean dose limit for the OAR according to an embodiment of the present invention.

Another example of a modification technique pertains to a situation where the original treatment objective for the OAR is specified in terms of a mean dose limit for the OAR volume. For example, the original treatment objective for OAR 604 might be: "the mean dose for the OAR should not exceed 30 Gy." FIG. 10 shows a flow diagram of a process 1000 for determining modified treatment objectives when an original treatment objective specifies a mean dose limit for the OAR according to an embodiment of the present invention. Process 1000 can be implemented, e.g., at block 710 of process 700. Process 1000 assumes that the OAR/target overlap region should receive higher than the originally-specified mean dose, from which it follows that a lower mean dose limit should be applied to the OAR-only region, such that the mean across the entire OAR satisfies the original treatment objective.

More specifically, at block 1002, process 1000 determines a mean dose for OAR/target overlap region 854, e.g., based on the original treatment objective for target structure 602. For instance, process 1000 may assume that OAR/target overlap region 854 will receive a mean dose equal to the lower bound or the midpoint of the dose range for target structure 602. At block 1004, process 1000 determines a mean dose for OAR/margin overlap region 853, e.g., based on the original treatment objective for target structure 602 and information about predicted ramp behavior of the treatment machine in margin regions around a target structure. For instance, falloff of beam intensity may have a known profile such that the dose in margin region 802 can be approximately predicted as a fraction of the target dose. At block 1006, process 1000 computes the volume occupied by each of OAR/target overlap region 854, OAR/margin overlap region 853, and OAR-only region 851. At block 1008, a mean dose for OAR-only region 851 is computed based on these volumes, the mean doses determined at blocks 1002 and 1004, and the mean dose specified in the original treatment objective. At block 1010, modified treatment objectives are defined based on the mean doses: for OAR/target overlap region 854, the modified treatment objective is based on the mean dose determined at block 1002; for OAR/margin overlap region 853, the modified treatment objective is based on the mean dose determined at block 1004; for OAR-only region 851, the modified treatment objective is based on the mean dose determined at block 1008.

By way of numerical example, suppose that the original treatment objective for OAR 604 specifies that the mean dose should be not more than 30 Gy, and the original treatment objective for target structure 602 specifies that 100% of target structure 602 should receive a dose of between 50 Gy and 51 Gy. At block 1002, process 1000 determines that the mean dose for OAR/target overlap region 854 is 50.5 Gy. At block 1004, process 1000 determines based on ramp behavior of a particular machine that the mean dose for OAR/margin overlap region 853 is, e.g., 40 Gy. At block 1006, process 1000 determines the volumes of the various regions. For purposes of illustration, suppose that OAR/target overlap region 854 occupies 20% of the volume of OAR 604, OAR/margin overlap region 853 occupies 10%, and OAR-only region 851 occupies 70%. At block 1008, process 1000 can compute that a mean dose of 22.7 Gy in OAR-only region 851 would result in a mean dose of 30 Gy for all of OAR 604. Accordingly, the modified treatment objectives can be set as: mean dose for OAR/target overlap region 854 should not exceed 50.5 Gy; mean dose for OAR/margin overlap region 853 should not exceed 40 Gy; mean dose for OAR-only region 851 should not exceed 22.7 Gy (which is lower than the originally-specified 30 Gy).

Those skilled in the art will appreciate that other processes for defining modified treatment objectives can be used at block 710 of process 700, in addition to or instead of the examples in FIGS. 9 and 10. As noted above, the general principle can be to allow the dose in the overlap regions to be higher than the original treatment objective for the OAR while reducing the allowed dose in the OAR-only region such that the overall dose to the OAR meets the original treatment objective. It should also be noted that processes such as processes 900 and 1000 can also be applied in instances where the treatment objectives for two overlapping structures are not mathematically incompatible. For instance, applying a tighter upper limit to a region of a target structure that overlaps with an OAR may be desirable to avoid the occurrence of hot spots (localized high dose) in that region while allowing higher doses in other portions of the target structure.

Referring again to FIG. 7, after determining modified treatment objectives at block 710, process 700 can generate a treatment plan using the modified treatment objectives and the modified regions in place of the original treatment objectives for the target structure and OAR. Generation of a treatment plan can incorporate conventional techniques, such as an interactive user interface to allow the user to modify the cost function, e.g., by modifying the weights associated with various treatment objectives. In some embodiments, the user may be able to view and/or adjust the modified treatment objectives (or their associated weights). Once a treatment plan is generated, process 700 can end. Thereafter, the treatment plan can be used to control operation of radiation treatment system 100 (or radiation treatment system 500) to perform a radiation treatment on the patient. For instance, in embodiments where process 700 is implemented in control circuitry 560, control circuitry 560 can be instructed by the user to perform the radiation treatment in accordance with the deliverable plan. In embodiments where process 700 is implemented on a different computer system, the treatment plan can be represented in a computer-readable format (e.g., a configuration file conforming to a particular syntax) and delivered to control circuitry 560 using any available data-transfer mechanism (e.g., network transfer, removable storage medium). Control circuitry 560 can read and execute the treatment plan. Executing the treatment plan can include operating the beam source, movable gantry, and MLC in accordance with machine parameters specified in the treatment plan to deliver radiation to a patient.

Overlap Among More than Two Structures

Figure 11A:
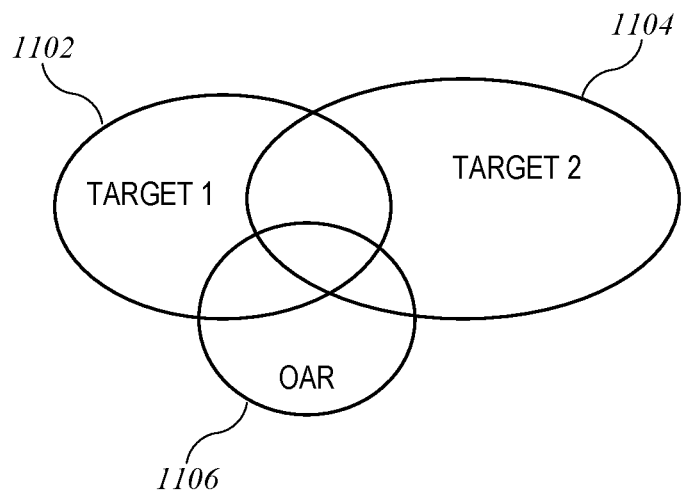
FIG. 11A is a simplified diagram illustrating a case where three treatment objectives may conflict.
Figure 11B:
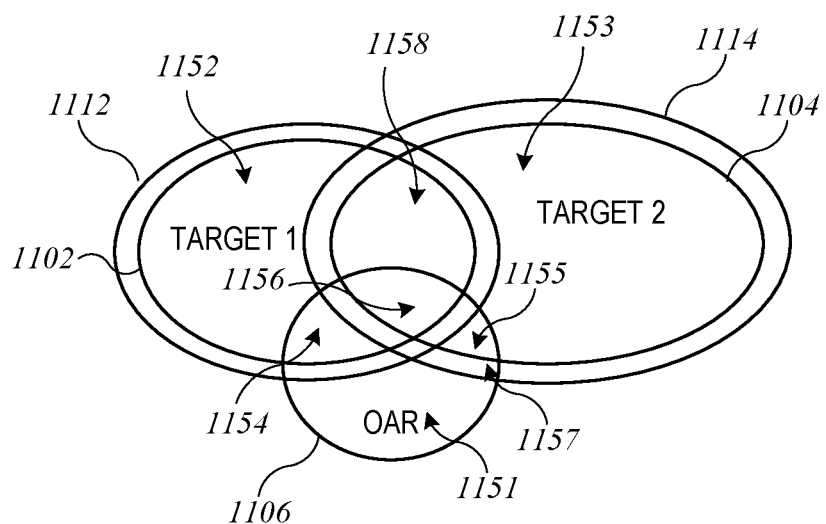
FIG. 11B shows an example of modified regions that may be defined for the case shown in FIG. 11A

In some embodiments, there may be overlap among more than two structures. For example, FIG. 11A is a simplified diagram illustrating a case where three treatment objectives may conflict. Shown are a first target structure 1102, a second target structure 1104, and an OAR 1106, as seen in a plane transverse to an expected beam direction. Such cases can be handled similarly to the case shown in FIGS. 6 and 8A-8B, except that defining more regions of interest may be useful. FIG. 11B shows an example of regions that may be defined for the case shown in FIG. 11A, including margins 1112 and 1114 around first and second target structures 1102, 1104. The regions of interest include: (1) An "OAR only" region 1151 that includes the portion of OAR 1106 that does not overlap with either of target structures 1102, 1104 or their margins 1112, 1114; (2) a "T1-only" region 1152 that includes the portion of target structure 1102 (but not margin 1112) that does not overlap with any other structure; (3) a "T2-only" region 1153 that includes the portion of target structure 1104 (but not margin 1114) that does not overlap with any other structure; (4) an "OAR/T1" overlap region 1154 that includes the portion of OAR 1106 that overlaps with first target structure 1102 but not second target structure 1104; (5) an "OAR/T2" overlap region 1155 that includes the portion of OAR 1106 that overlaps with second target structure 1104 but not first target structure 1102; (6) an "OAR/T1/T2" overlap region 1156 that includes the portion of OAR 1106 that overlaps with both T1 and T2; (7) an "OAR/margin" overlap region 1157 that includes the portion of OAR 1106 that overlaps only with the margins 1112 and/or 1114; and (8) a "T1/T2" overlap region 1158 that includes the portions of first target structure 1102 and second target structure 1104 that overlap with each other. Additional regions can also be defined if desired; for instance, the OAR/T1 margin may be treated separately from the OAR/T2 margin. Further, regions where one target structure overlaps with the margin of the other target structure can be treated separately from other regions.

Assuming that each of first target structure 1102, second target structure 1104, and OAR 1106 has a different treatment objective, the same principles described above can be used to determine modified treatment objectives for OAR-only region 1151, OAR/T1 overlap region 1154 (where second target structure 1104 can be ignored), and OAR/T2 overlap region 1155 (where first target structure 1102 can be ignored). The modified treatment objectives for T1-only region 1152 and T2-only region 1153 can be the same as the original treatment objectives for the corresponding target structures 1102, 1104. For T1/T2 overlap region 1158, a simple rule can be applied; for instance, the treatment objective that specifies the higher dose limit is applied to T1/T2 overlap region 1158. OAR/margin overlap region 1157 can be treated similarly to OAR/margin overlap region 853 described above; for this purpose, the two target structures can be treated as a single target having the treatment objective of T1/T2 overlap region 1158. Alternatively, OAR/margin overlap region 1157 can be further divided into a region of overlap with the margin of T1, a region of overlap with the margin of T2, and a region of overlap with both margins; and each of these regions can be treated similarly to OAR/margin overlap region 853 described above.

It should also be understood that an OAR can overlap with two or more disjoint targets. This case can be treated similarly to the examples above, except that there would not be a target/target overlap region. Similarly, two targets may overlap with each other, and this case can be handled similarly to T1/T2 overlap region 1108.

Dynamic Margins

As noted above, margins can be defined around target structures (or other structures) to provide a region where the dose can ramp up (or down) from one dose level (e.g., the dose level for an OAR) to another (e.g., the dose level for a target structure). A margin can be based on physical parameters of a particular beam and radiation field. In some embodiments, margins around target structures can be defined statically, e.g., based on typical beam/field behavior. However, it may be possible to further improve the modeling of dose delivery for a given beam/field configuration by tailoring (or dynamically defining) the margins based on the parameters for a particular treatment. For example, a margin can be defined as a function of location (r) inside the patient's body and a set of field parameters representing the radiation field geometry.

In one example, margins can be based on the type of particle in the beam (e.g., photons, protons, electrons) and the energy of the particle. The margin in a direction lateral to the beam (or lateral to the plane of possible beam directions in the case of a beam delivered from a rotatable gantry) may be different from the margin in the longitudinal direction (i.e., direction of beam propagation). For instance, for photons having energy 6 MeV, the margin in the lateral direction can be 5 mm while the margin in the longitudinal direction is 3 mm. A lookup table can be constructed for various combinations of particle type and energy, and the lookup table can be used for defining margins, e.g., at block 706 of process 700 described above.

Figure 12A:
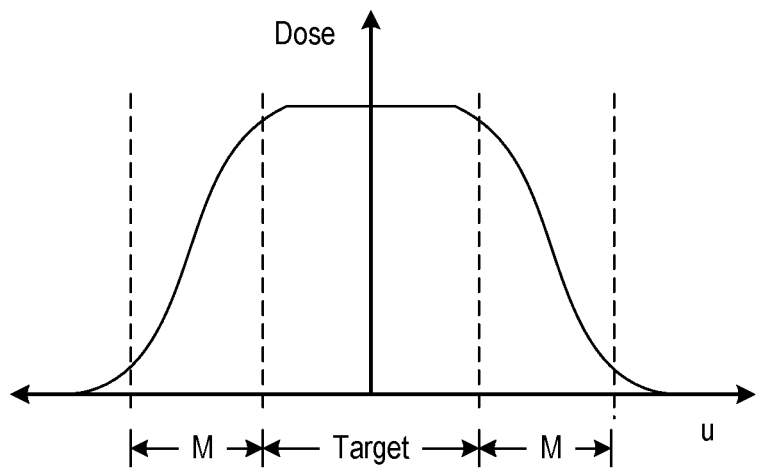
FIG. 12A shows schematically a graph of beam intensity as a function of position in a transverse direction around a target structure.
Figure 12B:
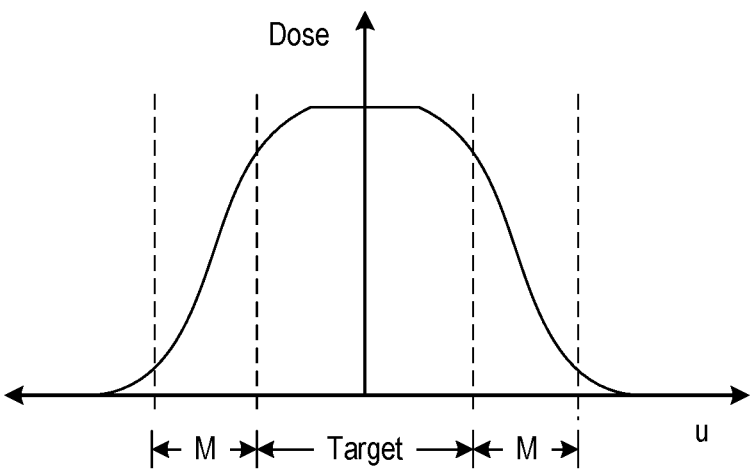
FIG. 12B shows an effect of relaxing a uniformity requirement relative to FIG. 12A.

In another example, margins can be pre-calculated for a target structure at a given location r within a patient's body, taking into account the number of fields and the uniformity requirement for the dose delivered to the target structure. FIG. 12A shows schematically a graph of dose profile in a medium (e.g., water phantom) as a function of position in a lateral direction (u) around a target structure having a particular width in the u-direction as shown. Margins (M) at either side of the target are indicated and extend from the edge of the target to a point where the dose reaches a low (e.g., non-damaging) level. In some embodiments, the width of margins M depends in part on the uniformity requirement for the dose delivered to the target structure. FIG. 12B shows an effect of relaxing the uniformity requirement relative to FIG. 12A. The relaxed uniformity requirement allows the width of the region of maximum dose to be reduced so that the dose falloff starts closer to the center of the target, which allows for narrower margins. As in the example above, a lookup table can be constructed for a given beam type to specify appropriate margins based on location r and uniformity requirements for the dose delivered to the target structure, and the lookup table can be used for defining margins, e.g., at block 706 of process 700 described above.

Figure 12C:
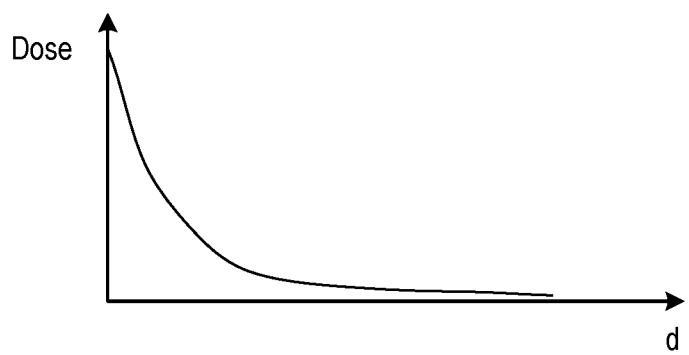
FIG. 12C shows an example of dose falloff with depth in a medium.

In another example, margins at the "front" surface of the target structure (i.e., where the beam enters) and the "back" surface of the target structure (i.e., where the beam exits) can be different, reflecting the absorption of particles as they pass through tissue. FIG. 12C shows an example of dose falloff with depth (d) in a medium (e.g., water phantom). In some embodiments, in therapies where the number of different beam directions used is small (e.g., proton or electron therapies), it may be desirable to provide a large front-surface margin and a small (or zero) back-surface margin. In therapies where beam from many directions is used (e.g., photon therapies), distinguishing front and back surfaces may not be useful and the margin can be uniform in different directions.

In still another example, in instances where relatively few fields are to be used, the beam geometry can be used to predict a dose shape around the target structure, and the dose shape can be used to define a margin around the target structure.

Computer System Implementation

Figure 13:
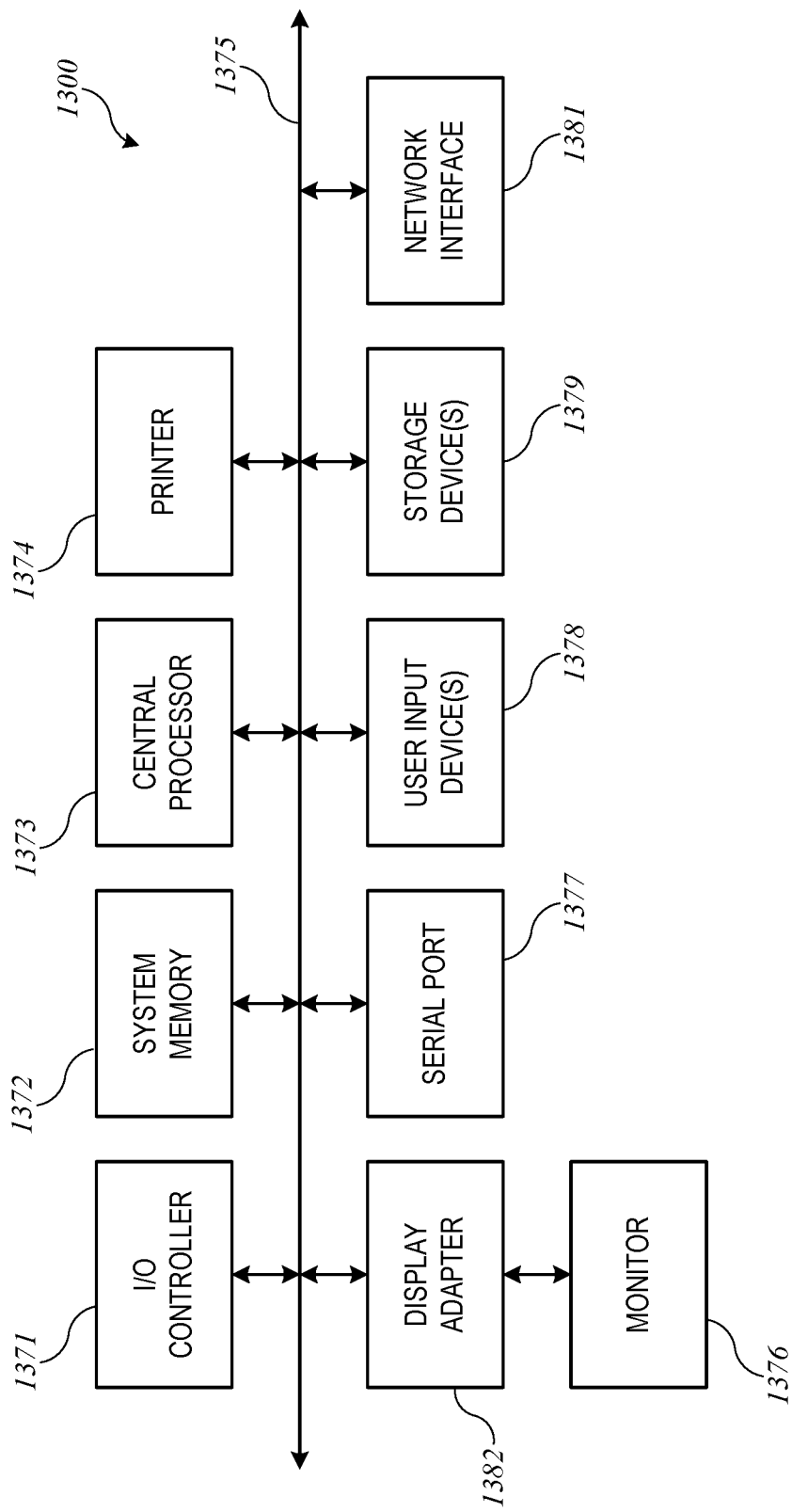
FIG. 13 shows a simplified block diagram of a computer system suitable for use in some embodiments of the present invention.

Processes described herein can be implemented in computer systems of various designs. FIG. 13 shows a simplified block diagram of a computer system 1300 suitable for use in some embodiments of the present invention. Computer system 1300 includes a number of different subsystems interconnected via a system bus 1375. The core subsystems include an input/output (I/O) controller 1371, a system memory 1372 (e.g., DRAM, SRAM, PROM, and/or other computer-readable media), and a central processor 1373. Central processor 1373, which can be implemented using one or more programmable integrated circuits (including single-core and/or multi-core microprocessors) controls operations of computer system 1300 by executing program code that can be stored (at least temporarily) in system memory 1372. Accordingly, central processor 1373 can communicate with each subsystem and can control the execution of instructions from system memory 1372 or storage device(s) 1379, as well as the exchange of information between subsystems. Similarly, any of the data mentioned herein can be delivered from one component to another component and can be output to (or input from) the user. In some embodiments, central processor 1373 may be coupled to one or more coprocessors, such as one or more graphics processing units (not shown) that are designed for high-throughput parallel processing.

I/O controller 1371 allows other components to be communicatively coupled to central processor 1373, and central processor 1373 can receive input from other components and/or send output to other components via I/O controller 1371. Accordingly, additional subsystems such as printer 1374; user input device(s) 1378 (e.g., keyboard, mouse, etc.); storage device(s) 1379 (e.g., various computer-readable media such as hard disk drives or other fixed storage devices, removable disks, removable solid-state memory devices such as USB thumb drives, etc.); monitor 1376, which is coupled to display adapter 1382; and the like may be communicably coupled to central processor 1373. Peripherals and I/O devices, which may couple to I/O controller 1371, can be connected to the computer system using various interconnect standards known in the art, such as serial port 1377. Wireless local-area connectivity (e.g., via Bluetooth or Wi-Fi or the like) may also be supported.

In some embodiments, network interface 1381 may be provided to enable communication between computer system 1300 and other computer systems, e.g., via Ethernet, Wi-Fi, or the like. Network interface 1381 may support connection to a local area network and/or to a wide-area network such as the internet. Thus, for example, process 700 and other processes described herein can be implemented in one instance of computer system 1300, which can communicate treatment plans to another instance of computer system 1300 local to radiation treatment system 100 (e.g., including control circuitry 560).

In some embodiments, computer system 1300 is implemented as a single computer apparatus with some or all of the subsystems described above. In some embodiments, a single instance of computer system 1300 can include multiple instances of the same components or subsystems, e.g., connected together by an internal interface. In some embodiments, two or more instances of computer system 1300 (which can be configured alike or differently as desired) can communicate over a network. In such embodiments, one instance can be considered a client and another instance a server.

Various features described herein, e.g., methods, apparatus, computer-readable media and the like, can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Any of the software-implemented components or functions described in this application may be realized in the form of software code to be executed by a processor; such code may be created using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may also be a combination of multiple such media.

Such programs may also be encoded and transmitted using carrier signals adapted for transmission via wired, optical, and/or wireless networks conforming to a variety of protocols, including the Internet. (It is noted that "storage" of programs or data is distinct from propagation of programs or data using transitory media such as carrier waves.) Computer readable storage media encoded with the program code may be packaged with a compatible device or provided separately from other devices (e.g., as a separately packaged computer readable storage medium or via an internet download operation that results in the program code being stored on a computer readable storage medium of the device that downloaded it). Any such computer readable medium may reside on or within a single computer product (e.g. a hard drive, a CD, or an entire computer system), and may be present on or within different computer products within a system or network.

Any of the methods described herein may be totally or partially performed with a computer system including one or more processors, which can be configured to perform the steps. Thus, embodiments of the present invention can include computer systems configured to perform the steps of any of the methods described herein, potentially with different components performing different steps or different groups of steps.

Further Embodiments

While the invention has been described with reference to specific embodiments, those skilled in the art will appreciate that variations and modifications are possible and that specific embodiments described herein are intended as illustrative and not limiting. All processes described herein are illustrative, and variations and modifications are possible. Except where internal logic requires a particular order, operations or blocks described sequentially may be executed in parallel, order of operations may be varied, and operations described in connection with different blocks can be combined. Further, it is not necessary that every operation described herein be performed in every embodiment of the invention; some operations can be omitted, and other operations not specifically described herein may be added. Techniques described herein for automatically defining a margin around a target structure may also be applied outside the particular context of resolving conflicting treatment objectives, including any instance in a treatment planning process where it is desirable to specify a margin around a target structure, e.g., for purposes of modeling dose ramp-up (or ramp-down).

The foregoing description references specific conflict situations such as where a target structure and an OAR overlap and have conflicting treatment objectives. It should be understood that conflicts are not limited to instances of overlap between a target structure and an OAR; other instances of overlapping structures may give rise to conflicts as well. For instance, a first target structure may overlap with a second target structure, and the treatment objective for the first target structure may specify a dose range that does not overlap with the dose range for the second target structure. As another (rare but possible) example, a first OAR may overlap with a second OAR, and the treatment objective for the first OAR may prescribe a specific minimum dose level that is higher than a maximum dose level prescribed for the second OAR. Any such conflicts can be addressed using processes of the kind described above. Further, even in instances where it is not mathematically impossible to satisfy both treatment objectives in an overlap region, modification of the regions and treatment objectives in the manner described herein may be used to refine treatment objectives for overlapping structures.

As another example, in some embodiments described above, a margin is defined around the target structure, with a portion of the margin overlapping the OAR. In clinical practice, defining the margin around the target structure makes it more likely that all of the target tissue will receive a therapeutically effective dose of radiation. However, in some instances, protecting the OAR from damaging levels of radiation exposure may be a higher-priority goal than irradiating every portion of the target structure; one example would be where the OAR is the spinal cord (or a portion thereof). In such cases, the margin can be drawn around the OAR, with a portion of the margin overlapping the target region. Conflict-resolution processes of the kind described above can be applied, except that instead of an OAR/margin overlap region, there would be a target/margin overlap region that can be handled similarly to the OAR/margin overlap region as described above.

Thus, while the invention has been described with reference to specific embodiments, it is to be understood that the invention is defined by the following claims.

What is claimed is:

1. A computer implemented method for radiation therapy treatment planning, the method comprising:
  receiving, at a computer system, input defining a plurality of regions including a first structure and a second structure and an original treatment objective for each of the regions, the original treatment objectives including a first original treatment objective for the first structure and a second original treatment objective for the second structure, wherein the first original treatment objective specifies an original lower limit on a dose received by the first structure and the second original treatment objective specifies an original upper limit on a dose received by the second structure, wherein the original lower limit is higher than the original upper limit;
  detecting, by the computer system, a geometric overlap between the first structure and the second structure;
  defining, by the computer system, a margin around the first structure;
  defining, by the computer system, a plurality of modified regions including:
    a first modified region that includes any portion of the second structure that does not overlap with the first structure or the margin,
    a second modified region that includes any portion of the first structure that does not overlap with the second structure,
    a third modified region that includes any portion of the second structure that overlaps with the margin, and
    a fourth modified region that includes any portion of the second structure that overlaps with the first structure;
  determining, by the computer system, a set of modified treatment objectives including a first modified treatment objective for the first modified region, a second modified treatment objective for the second modified region, a third modified treatment objective for the third modified region, and a fourth modified treatment objective for the fourth modified region, wherein the modified treatment objectives are determined based on the first original treatment objective and the second original treatment objective and wherein the first modified treatment objective specifies a modified upper limit on a dose received by the first modified region that is lower than the original upper limit; and
  using, by the computer system, the plurality of modified regions and the set of modified treatment objectives in a treatment planning process to generate a treatment plan for treating a patient.

2. The method of claim 1 wherein the first structure corresponds to a target structure and the second structure corresponds to an organ at risk.

3. The method of claim 1 wherein defining the margin includes accessing a lookup table using a beam type parameter and a beam energy parameter to retrieve a corresponding margin.

4. The method of claim 1 wherein defining the margin includes accessing a lookup table using a beam type, a location of the first structure within the patient's body, and a uniformity requirement determined from the first original treatment objective to retrieve a corresponding margin.

5. The method of claim 1 wherein defining the margin includes defining a front margin for a forward surface of the first structure and a rear margin for a rearward surface of the first structure, wherein the front margin is larger than the rear margin.

6. The method of claim 1 wherein defining the margin includes:
  predicting a dose shape around the first structure based on a beam geometry model; and
  defining the margin based on the predicted dose shape.

7. The method of claim 1 wherein determining the modified treatment objectives includes allowing a dose received by the fourth modified region and the third modified region to exceed the original upper limit.

8. The method of claim 1 wherein the the original upper limit specifies a maximum mean dose to be delivered to the second structure and wherein determining the modified treatment objectives includes:
  allowing the fourth modified region to receive a dose consistent with the first original treatment objective;
  determining an allowed dose for the third modified region based on a ramp up behavior; and
  determining an allowed dose for the first modified region that is lower than the original upper limit such that the mean dose across the fourth modified region, the third modified region, and the first modified region does not exceed the maximum mean dose.

9. The method of claim 1 further comprising:
operating a radiation treatment system in accordance with the treatment plan to perform a radiation treatment on a patient.

10. The method of claim 9 wherein the treatment plan includes a control point sequence and a multileaf collimator leaf sequence and wherein operating the radiation treatment system in accordance with the treatment plan includes:
providing, by a treatment head of the radiation treatment system coupled with a radiation source, radiation at one or more angles specified by the control point sequence and using a sequence of movements of a multileaf collimator specified by the multileaf collimator leaf sequence, such that radiation in accordance with the treatment plan is delivered to the first structure and the second structure.

11. A computer implemented method for radiation therapy treatment planning, the method comprising:
receiving, at a computer system, input defining a plurality of regions including a first structure and a second structure and an original treatment objective for each of the regions, the original treatment objectives including a first original treatment objective for the first structure and a second original treatment objective for the second structure, wherein the first original treatment objective is inconsistent with the second original treatment objective and wherein the second original treatment objective specifies a maximum volumetric percentage of the second structure that should receive a dose above an upper limit;
detecting, by the computer system, a geometric overlap between the first structure and the second structure;
defining, by the computer system, a margin around the first structure;
defining, by the computer system, a plurality of modified regions including:
a first modified region that includes any portion of the second structure that does not overlap with the first structure or the margin,
a second modified region that includes any portion of the first structure that does not overlap with the second structure,
a third modified region that includes any portion of the second structure that overlaps with the margin, and
a fourth modified region that includes any portion of the second structure that overlaps with the first structure;
determining, by the computer system, a set of modified treatment objectives including a first modified treatment objective for the first modified region, a second modified treatment objective for the second modified region, a third modified treatment objective for the third modified region, and a fourth modified treatment objective for the fourth modified region, wherein the modified treatment objectives are determined based on the first original treatment objective and the second original treatment objective and wherein determining the modified treatment objectives includes:
determining a volumetric percentage of the second structure that has been assigned to the third modified region or the fourth modified region;
in the event that the volumetric percentage of the second structure that has been assigned to the third modified region or the fourth modified region is less than the maximum volumetric percentage of the second structure, allowing the third modified region and the fourth modified region to receive a dose above the upper limit and allowing a correspondingly reduced volumetric percentage of the first modified region to receive a dose above the upper limit; and
in the event that the volumetric percentage of the second structure that has been assigned to the third modified region or the fourth modified region is greater than the maximum volumetric percentage of the second structure, allowing the fourth modified region and a portion of the third modified region to receive a dose above the upper limit and allowing no portion of the first modified region to receive a dose above the upper limit; and
using, by the computer system, the plurality of modified regions and the set of modified treatment objectives in a treatment planning process to generate a treatment plan for treating a patient.

12. A system comprising:
a memory; and
a processor coupled to the memory and configured to:
receive input defining a plurality of regions including a first structure and a second structure and an original treatment objective for each of the regions, the original treatment objectives including a first original treatment objective for the first structure and a second original treatment objective for the second structure, wherein the first original treatment objective specifies an original lower limit on a dose received by the first structure and the second original treatment objective specifies an original upper limit on a dose received by the second structure, wherein the original lower limit is higher than the original upper limit;
detect a geometric overlap between the first structure and the second structure;
define a margin around the first structure;
define a plurality of modified regions including:
a first modified region that includes any portion of the second structure that does not overlap with the first structure or the margin;
a second modified region that includes any portion of the first structure that does not overlap with the second structure,
a third modified region that includes any portion of the second structure that overlaps with the margin, and
a fourth modified region that includes any portion of the second structure that overlaps with the first structure;
determine a set of modified treatment objectives including a first modified treatment objective for the first modified region, a second modified treatment objective for the second modified region, a third modified treatment objective for the third modified region, and a fourth modified treatment objective for the fourth modified region, wherein the modified treatment objectives are determined based on the first original treatment objective and the second original treatment objective and wherein the first modified treatment objective specifies a modified upper limit on a dose received by the first modified region that is lower than the original upper limit; and
use the plurality of modified regions and the set of modified treatment objectives in a treatment planning process to generate a treatment plan for treating a patient.

13. The system of claim 12 wherein the first structure corresponds to a target structure and the second structure corresponds to an organ at risk.

14. The system of claim 12 wherein the processor is further configured such that defining the margin includes accessing a lookup table using a beam type parameter and a beam energy parameter to retrieve a corresponding margin.

15. The system of claim 12 wherein the processor is further configured such that defining the margin includes accessing a lookup table using a beam type, a location of the first structure within the patient's body, and a uniformity requirement determined from the first original treatment objective to retrieve a corresponding margin.

16. The system of claim 12 wherein the processor is further configured such that defining the margin includes defining a front margin for a forward surface of the first structure and a rear margin for a rearward surface of the first structure, wherein the front margin is larger than the rear margin.

17. The system of claim 12 wherein the processor is further configured such that defining the margin includes:
predicting a dose shape around the first structure based on a beam geometry model; and
defining the margin based on the predicted dose shape.

18. The system of claim 12 wherein the processor is further configured such that determining the modified treatment objectives includes allowing a dose received by the fourth modified region and the third modified region to exceed the original upper limit.

19. The system of claim 12 wherein the the original upper limit specifies a maximum mean dose to be delivered to the second structure and wherein the processor is further configured such that determining the modified treatment objectives includes:
allowing the fourth modified region to receive a dose consistent with the first original treatment objective;
determining an allowed dose for the third modified region based on a ramp up behavior; and
determining an allowed dose for the first modified region that is lower than the original upper limit such that the mean dose across the fourth modified region, the third modified region, and the first modified region does not exceed the maximum mean dose.

20. The system of claim 12 wherein the processor is further configured to:
operate a radiation treatment system in accordance with the treatment plan to perform a radiation treatment on a patient.

21. The system of claim 20 further comprising:
a treatment head coupled with a radiation source; and
a multileaf collimator,
wherein the processor is further configured such that operating the radiation treatment system in accordance with the treatment plan includes providing, by the treatment head, radiation from the radiation source at one or more angles specified by the treatment plan and using a sequence of movements of the multileaf collimator specified by the treatment plan, such that radiation in accordance with the treatment plan is delivered to the first structure and the second structure.

22. A system comprising:
a memory; and
a processor coupled to the memory and configured to:
receive input defining a plurality of regions including a first structure and a second structure and an original treatment objective for each of the regions, the original treatment objectives including a first original treatment objective for the first structure and a second original treatment objective for the second structure, wherein the first original treatment objective is inconsistent with the second original treatment objective and wherein the second original treatment objective specifies a maximum volumetric percentage of the second structure that should receive a dose above an upper limit;
detect a geometric overlap between the first structure and the second structure;
define a margin around the first structure;
define a plurality of modified regions including:
a first modified region that includes any portion of the second structure that does not overlap with the first structure or the margin;
a second modified region that includes any portion of the first structure that does not overlap with the second structure,
a third modified region that includes any portion of the second structure that overlaps with the margin, and
a fourth modified region that includes any portion of the second structure that overlaps with the first structure;
determine a set of modified treatment objectives including a first modified treatment objective for the first modified region, a second modified treatment objective for the second modified region, a third modified treatment objective for the third modified region, and a fourth modified treatment objective for the fourth modified region, wherein the modified treatment objectives are determined based on the first original treatment objective and the second original treatment objective and wherein the processor is further configured such that determining the modified treatment objectives includes:
determining a volumetric percentage of the second structure that has been assigned to the third modified region or the fourth modified region;
in the event that the volumetric percentage of the second structure that has been assigned to the third modified region or the fourth modified region is less than the maximum volumetric percentage of the second structure, allowing the third modified region and the fourth modified region to receive a dose above the upper limit and allowing a correspondingly reduced volumetric percentage of the first modified region to receive a dose above the upper limit; and
in the event that the volumetric percentage of the second structure that has been assigned to the third modified region or the fourth modified region is greater than the maximum volumetric percentage of the second structure, allowing the fourth modified region and a portion of the third modified region to receive a dose above the upper limit and allowing no portion of the first modified region to receive a dose above the upper limit; and
use the plurality of modified regions and the set of modified treatment objectives in a treatment planning process to generate a treatment plan for treating a patient.

* * * * *

UNITED STATES PATENT AND TRADEMARK OFFICE
CERTIFICATE OF CORRECTION

PATENT NO. : 10,828,509 B2
APPLICATION NO. : 15/895892
DATED : November 10, 2020
INVENTOR(S) : Jarkko Peltola et al.

It is certified that error appears in the above-identified patent and that said Letters Patent is hereby corrected as shown below:

In the Claims

In Column 20, Line 55, in Claim 8, replace "the the" with --the--.

In Column 23, Line 30, in Claim 19, replace "the the" with --the--.

Signed and Sealed this
Nineteenth Day of January, 2021

Andrei Iancu
*Director of the United States Patent and Trademark Office*